United States Patent
Nessel et al.

(10) Patent No.: US 10,842,939 B2
(45) Date of Patent: Nov. 24, 2020

(54) PRESSURE CONTAINER FOR DRIVING A MEDICAL DEVICE

(71) Applicant: SANOFI-AVENTIS DEUTSCHLAND GMBH, Frankfurt am Main (DE)

(72) Inventors: Christian Nessel, Frankfurt am Main (DE); Christian Dexheimer, Rüsselsheim (DE); Tobias Uth, Rüsselsheim (DE); Florian Hammen, Rüsselsheim (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 438 days.

(21) Appl. No.: 15/571,691

(22) PCT Filed: May 6, 2016

(86) PCT No.: PCT/EP2016/060146
§ 371 (c)(1),
(2) Date: Nov. 3, 2017

(87) PCT Pub. No.: WO2016/180719
PCT Pub. Date: Nov. 17, 2016

(65) Prior Publication Data
US 2018/0147354 A1    May 31, 2018

(30) Foreign Application Priority Data
May 8, 2015   (EP) ...................... 15166871

(51) Int. Cl.
*A61M 5/20* (2006.01)
*F04B 9/12* (2006.01)
(Continued)

(52) U.S. Cl.
CPC ...... *A61M 5/2046* (2013.01); *A61M 5/14276* (2013.01); *A61M 5/155* (2013.01);
(Continued)

(58) Field of Classification Search
CPC .......... A61M 2005/14513; A61M 2005/2013; A61M 5/155; A61M 5/2046; A61M 5/2053; A61M 5/14276
See application file for complete search history.

(56) References Cited

U.S. PATENT DOCUMENTS 3,122,284 A * 2/1964 Wayne ................. B65D 83/663
                                                  222/399
4,561,856 A * 12/1985 Cochran ............... A61M 5/155
                                                  604/143
(Continued)

FOREIGN PATENT DOCUMENTS

WO    WO 2011/153261    12/2011

OTHER PUBLICATIONS

International Search Report and Written Opinion in International Application No. PCT/EP2016/060146, dated Jul. 19, 2016, 9 pages.
(Continued)

*Primary Examiner* — Brandy S Lee
(74) *Attorney, Agent, or Firm* — Fish & Richardson P.C.

(57) ABSTRACT

The present disclosure relates to a portable pressure container for driving a medical device. The container includes a pressure housing confining an interior volume and a pressure outlet extending through the pressure housing. The interior volume comprises a liquid storage portion and a gas storage portion. The liquid storage portion and the gas storage portion are in flow connection with each other. The liquid storage portion is configured to store a liquid phase of a driving medium. The gas storage portion is configured to store a gas phase of the driving medium. The pressure outlet is only in flow connection with the gas storage portion.

15 Claims, 4 Drawing Sheets (51) Int. Cl.
  *A61M 5/155* (2006.01)
  *A61M 5/142* (2006.01)
  *A61M 5/145* (2006.01)

(52) U.S. Cl.
  CPC ............. *A61M 5/2053* (2013.01); *F04B 9/12* (2013.01); *A61M 2005/14513* (2013.01); *A61M 2005/2013* (2013.01)

(56) References Cited

U.S. PATENT DOCUMENTS

| | | |
|---|---|---|
| 4,773,900 A | 9/1988 | Cochran |
| 2012/0071829 A1 | 3/2012 | Edwards et al. |

OTHER PUBLICATIONS

International Preliminary Report on Patentability in International Application No. PCT/EP2016/060146, dated Nov. 14, 2017, 7 pages.

\* cited by examiner

PRESSURE CONTAINER FOR DRIVING A MEDICAL DEVICE

CROSS REFERENCE TO RELATED APPLICATIONS

The present application is the national stage entry of International Patent Application No. PCT/EP2016/060146, filed on May 6, 2016, and claims priority to Application No. EP 15166871.2, filed on May 8, 2015, the disclosures of which are expressly incorporated herein in entirety by reference thereto.

TECHNICAL FIELD

The present disclosure relates to the field of pressure containers and in particular to pressure containers for pressure driven medical devices such like automatic injection devices for delivery of a liquid medicament by way of injection.

BACKGROUND

Automatic medicament delivery devices, such like autoinjectors provide a rather easy and convenient approach to inject a predefined dose of a liquid medicament into biological tissue. Such drug delivery devices may provide an injection needle extension and retraction mechanism in order to puncture biological tissue to which the liquid medicament is to be delivered. After the injection needle has been extended into an injection position, drug delivery through the injection needle may automatically start. After termination of a delivery process the needle is typically retracted back into the housing. Since such drug delivery devices are intended for home or self-medication, their general handling should be easily understandable and unambiguous.

Additionally, such devices should provide a high degree of patient safety in order to avoid stitch damages or similar injuries. The therapy, the medication schedule, the size of the dose, and/or the viscosity of the liquid medicament may cause some difficulties and problems with existing drug delivery device designs. For instance, the total time for the delivery of the medicament may be out of a predefined range. This can occur, in some cases, when the injection volume is rather large, e.g., larger than 1.25 ml and/or when the liquid medicament has a high viscosity. Alternatively, a high viscosity and a large volume of the liquid medicament could lead to patient discomfort.

When such drug delivery or injection devices are of portable or mobile type, they are typically equipped with some kind of energy storage to conduct a dispensing procedure and optionally to displace and to retract the injection needle. Document US 2012/0071829 A1 describes an apparatus featuring a medicament injector moveably disposed within a housing and an energy storage member configured to produce a force to move the medicament injector to an injection position in which a portion of a needle is disposed outside of a distal end portion of the housing.

The energy storage member is a compressed gas cylinder that is operable to produce a force that acts upon the medicament container to move the medicament container between a first position and a second position. In response to a force produced by the pressurized gas, a moveable member and the medicament injector are moved towards a distal end portion of the housing, thereby exposing the needle from the housing. Thereafter a movable member continues to move a medicament container distally within a carrier. This continued movement of the medicament container places the needle in fluid communication with the medicament container, thereby allowing the medicament to be injected. Finally, the force from the pressurized gas causes the movable member to move within the medicament container, thereby expelling the medicament through the needle.

Energy storage by compressed gas comes along with some limitations in regards to the stability of the pressure of the gaseous driving medium as the compressed gas leaves the respective pressure container. Providing a constant pressure of the gaseous driving medium over a rather long time interval, e.g. over a complete time of injection either requires implementation of rather highly pressurized pressure containers or requires an increase of the size and the filling volume of such pressure containers. For mobile or portable medical applications both of these options come along with some drawbacks in regards to compact and small-sized portable medical devices or in view of patient safety and handling comfort.

SUMMARY

In a first aspect, a portable pressure container for driving a medical device is provided. The container comprises a pressure housing confining or defining an interior volume. The pressure container further has a pressure outlet extending through the pressure housing. The pressure outlet provides a flow or fluid connection between the exterior and the interior volume of the pressure housing. Typically, the pressure outlet comprises some kind of standardized adapter or connector by way of which the pressurized content of the pressure container can be guided or transferred to the medical device for driving the same.

The interior volume of the pressure housing comprises a liquid storage portion and a gas storage portion. The liquid storage portion and the gas storage portion are in flow connection with each other. Hence, a liquid phase of a driving medium located inside the liquid storage portion is free to evaporate into the gas storage portion and vice versa. Furthermore, the liquid storage portion is configured to store a liquid phase of a driving medium. In the same or similar way, the gas storage portion is configured to store a gas phase of the driving medium.

Typically, the interior volume of the pressure housing is substantially divided into the liquid storage portion and the gas storage portion. The driving medium is typically located inside the interior volume of the pressure housing, wherein its liquid phase is predominantly located inside the liquid storage medium and wherein its gas phase is typically provided in and completely fills the gas storage portion. Depending on the pressure and temperature inside the pressure housing the liquid phase and the gas phase of the driving medium are in a state of equilibrium. By modifying at least one of the pressure and the temperature the equilibrium can be arbitrarily shifted so that for instance at least 50 wt. % or more of the total driving medium is present in a liquid phase inside the pressure housing.

Moreover the pressure outlet of the portable pressure container is only or exclusively in flow connection with the gas storage portion of the interior volume. In this way, it is substantially guaranteed and assured that only the gas phase of the driving medium may leave the pressure container for driving the medical device, while the liquid phase of the driving medium is substantially hindered from leaving the pressure container.

With the portable pressure container to accommodate a liquid phase and a gas phase of a driving medium a rather constant driving pressure can be provided at the pressure outlet. As soon as the gas phase starts to emanate from the pressure housing via the pressure outlet a portion of the liquid phase of the driving medium evaporates into the gas phase. As a result, a rather constant gas pressure can be obtained at the pressure outlet for a comparatively long period of time. A rather constant gas pressure can be effectively provided at the pressure outlet as long as there is sufficient liquid phase of the driving medium inside the interior volume.

Typically, the portable pressure container is dedicated to be carried along by the patient thereby being thermally coupled to the patient. For instance, the medical device and hence the respective portable pressure container may be adhesively attached to the skin of the patient. Then, an enthalpy of evaporation of the driving medium from the liquid phase into the gas phase can be compensated by an inherent supply of thermal energy from the body of the patient, e.g. by way of the body heat of the patient. Moreover, it is also conceivable that the quantity of the liquid phase exceeds the quantity typically needed to drive the medical device. Then it is even conceivable that evaporation enthalpy is branched off from the liquid phase of the driving medium, thereby experiencing a slight cooling down as the gas phase escapes from the pressure container.

Having the pressure outlet exclusively in flow connection with the gas storage portion is beneficial to provide an orientation-independent extraction of the gaseous phase from the portable pressure container. From a technical point of view, the flow of the gaseous phase emanating from the pressure container is much easier to handle or to control compared to a liquid phase. Moreover, by way of storing a liquid phase to evaporate into a gas phase the working volume and hence the driving capability of the driving medium can be increased multiple times. By making use of a phase transition from a liquid phase towards a gas phase the storage capability in terms of providing a propellant gas can be increased without the necessity to increase the size of the portable pressure container.

According to another embodiment, the liquid storage portion is located remote and at a predefined non-zero distance from the pressure outlet. In addition, the gas storage portion is located between the liquid storage portion and the pressure outlet. In this way, the driving medium e.g. predominately provided in the liquid phase inside the interior volume first has to undergo a phase transition from the liquid phase into the gas phase. For this and depending on the various conceivable embodiments and geometries of gas storage portion and liquid storage portion, the liquid phase must be provided at or near a phase transition boundary between the liquid storage portion and the gas storage portion. Then, the liquid phase may at least partially or successively undergo a phase transition into the gas phase thereby maintaining a predefined gas pressure and an equilibrium inside the gas storage portion.

Arranging the gas storage portion between the liquid storage portion and the pressure outlet, prevents a portion of the liquid phase of the driving medium from entering the pressure outlet. In this way, the gas storage portion provides a geometric separation between the liquid storage portion and the pressure outlet.

The separation of the interior volume between the liquid storage portion and the gas storage portion may be of static or dynamic type. When implemented as a static separation at least one of the liquid storage portion and the gas storage portion comprises a geometrical structure that is particularly adapted to store only one of the liquid phase or the gas phase of the driving medium. When implemented dynamically it is conceivable, that the liquid storage portion and the gas storage portion are separated by a movable boundary whose geometric structure depends on a momentary position of the liquid phase and the gas phase. It is conceivable, that the boundary between the liquid phase and the gas phase is sensitive to gravity so that the boundary between liquid phase and gas phase is subject to dynamical changes as the orientation of the pressure container is modified.

In typical embodiments wherein the boundary between the liquid phase and the gas phase is of dynamic type, it is of particular benefit when the volume of the liquid phase of the driving medium is less than 60%, less than 50%, less that 40% or less than 30% of the interior volume of the pressure container. In this way it can be guaranteed that only the gas storage portion is in flow connection with the pressure outlet.

According to a further embodiment, a porous storage medium or a porous transport medium is arranged inside the liquid storage portion and extends towards or into the gas storage portion. When arranging a porous storage medium inside the interior volume, the entire liquid storage portion of the pressure container may be filled with or may even be defined by the porous storage medium. Typically, the porous storage medium is selected such, that the pores and the capillary attraction arising therefrom are configured to soak up or to absorb a major portion or even the entirety of the liquid phase of the driving medium. An outer edge or outer surface of the porous storage medium then defines the boundary between the liquid storage portion and the gas storage portion. Having a major portion of the driving medium absorbed in the porous storage medium inherently provides an orientation-independent extraction of the gaseous phase. Moreover, by making use of a porous storage medium the effective surface of the boundary between the liquid phase and the gas phase can be increased compared to an embodiment, wherein the surface of a filling level of the liquid phase defines said boundary.

When making use of a porous storage medium inside the interior volume it is the outer geometry and the surrounding volume of the porous storage medium that effectively defines the liquid storage portion of the interior volume. Typically, the residual portion of the interior volume then defines the gas storage portion.

In embodiments wherein a porous transport medium is located inside the interior volume, the transport medium is in flow connection with the liquid phase of the driving medium. It may be, for instance, immersed into the liquid phase of the driving medium. The porous transport medium is then at least with one end in fluid communication or in physical contact with the liquid phase whereas another end is in contact with or extends towards the gas storage portion.

With such an embodiment, it is generally conceivable to divide the liquid storage portion and the gas storage portion of the interior volume by a division structure, such like a division wall. It is then of particular benefit, when the division structure or division wall is intersected by the porous transport medium, thereby supporting a well-defined transport of the liquid phase of the driving medium out of the liquid storage portion and towards or into the gas storage portion. With such embodiments it is of particular benefit, when the porous transport medium extends almost through the entire liquid storage portion so that one end of the elongated porous transport medium is still in fluid connection with the liquid phase even if a considerable amount of the liquid phase has already left the liquid storage portion. An opposite end of the porous transport medium then typically extends into an evaporation chamber, which is either a portion of the gas storage portion or which is in direct flow communication with the gas storage portion.

According to a further embodiment, the porous storage medium is in abutment with an inner side of the pressure housing. In this way, the porous storage medium can be fixed to the pressure housing so as to provide a well-defined position and geometry of the liquid storage portion. By arranging the porous storage medium to an inner side, e.g. to a bottom portion or sidewall portion of the pressure housing, a thermal contact as well as a heat transfer from the exterior towards the porous storage medium can be improved. Moreover, by fixing and arranging the porous storage medium to the inside of the pressure housing a mutual contact between the pressure outlet and the porous storage medium, that could potentially lead to a clogging of the pressure outlet lead to can be effectively prevented.

According to another embodiment, the porous storage medium and the pressure outlet are arranged in or at opposite end sections of the pressure housing. In this way the distance between the porous storage medium and hence between the liquid storage portion and the pressure outlet can be maximized. In embodiments wherein the pressure container and its pressure housing comprise an elongated geometric structure, such like a tubular shape it is of particular benefit to arrange the pressure outlet and the porous storage medium at oppositely located longitudinal or axial ends of the pressure housing.

In a further embodiment, the porous storage medium is arranged on a bottom portion of the pressure housing and is held in place or is squeezed by a perforated grid. Typically, the porous storage medium is rather elastic and may require interaction with at least one fixing means to keep it rigidly fastened to the pressure housing. A perforated grid typically comprises numerous perforations in order to allow evaporation of the liquid phase stored in the porous storage medium. By means of the perforated grid, the porous storage medium may be sandwiched between the bottom portion of the pressure housing and the perforated grid. The perforated grid may be engageable with an inside of a sidewall portion of the pressure housing so as to fix the porous storage medium to the bottom portion. It is conceivable that the perforated grid is positively engageable with at least one fixing element or fixing structure located at the inside of the sidewall portion of the pressure housing. Alternatively, the perforated grid itself may be subject to squeezing, e.g. by means of a closure of the pressure housing or by means of a distance ring operably engageable with a closure of the pressure housing.

It is even conceivable to provide and to modify the degree of squeezing of the porous storage medium by varying the pressure acting on the perforated grid. In this way, a medium pore size as well as the overall geometric dimensions of the porous storage medium can be modified in general in order to modify a gas pressure level at the pressure outlet.

In another embodiment, the pressure outlet is located in an outlet member releasably engageable with the pressure housing. The outlet member effectively serves as a closure to close the pressure housing with regard to the exterior. The closure or outlet member is typically connectable with a top portion of the pressure housing located opposite the bottom portion thereof. In this way, the outlet member is inherently located at a maximum distance from the porous storage medium arranged on the opposite bottom portion. By means of a releasable or detachable outlet member, the pressure container may be refilled if necessary. Alternatively, the pressure container may be designed and configured as a disposable device that is discarded in its entirety once the medical device has been propelled by the driving medium.

In another embodiment, the outlet member comprises a sidewall threadedly engageable with a correspondingly threaded sidewall portion of the pressure housing. In this way, the outlet member may exert or induce a variable squeezing pressure onto the porous storage medium. Depending on the specific geometry of the outlet member, the pressure housing, the porous storage medium and/or of the perforated grid either a direct mechanical contact between the sidewall of the outlet member and the perforated grid is conceivable or the pressure container is further equipped with a distance member arranged between the sidewall of the outlet member and the perforated grid. Typically, the outer circumference of the outlet member's sidewall comprises an outer thread to mate and to engage with a correspondingly shaped inner thread of a correspondingly shaped sidewall portion of the pressure housing. At least one of the sidewalls or sidewall portions of outlet member and pressure housing is typically provided with a seal, such like an O-ring in order to provide a gas tight sealing of the interior volume with respect to the exterior. Additional or instead of an O-ring, a sealing tape may be wound along at least a portion of one of the threads of the sidewall of the pressure housing and the outlet member.

With the threaded engagement of the outlet member and the pressure housing, variable pressures can be applied to the porous storage medium in order to modify its liquid absorption capability and evaporation characteristics. A pressure acting on the porous storage medium can be arbitrarily and continuously modified by screwing or unscrewing the outlet member into the pressure housing.

According to another embodiment, the porous storage medium extends along a bottom portion and along a sidewall portion of the pressure housing. In other words, the porous storage medium extends almost along the entirety of the inward-facing portion of the pressure housing except a portion of the pressure housing located in direct vicinity to the pressure outlet. Given that the pressure housing is of elongated or cylindrical shape and that the pressure outlet is located at an upper longitudinal end of the pressure housing, the bottom portion as well as the sidewall portions of the pressure housing are, cladded, lined, or coated with the porous storage medium. Arranging of the porous storage medium to the inside of the wall structure of the pressure housing inherently provides a good thermal coupling to the exterior. If the medical device and/or its portable pressure container is, for instance, in thermal contact with the skin of a patient, evaporation enthalpy for the evaporation of the liquid phase into the gas phase can be easily extracted from the body heat.

The porous storage medium may provide a kind of a cladding at the inside of the pressure housing. With the porous storage medium extending along a bottom portion and along a sidewall portion of the pressure housing the gas storage portion of the interior volume is almost completely enclosed by the liquid storage portion.

According to a further embodiment, the entirety of the inside of the pressure housing is provided or covered by the porous storage medium. The pressure outlet may then comprise a fluid channel extending through and intersecting the porous storage medium so that one end of the pressure outlet is located inside the gas storage portion whereas an opposite end thereof is either accessible from outside or is located outside the pressure housing.

According to another embodiment, the porous storage medium comprises a self-supporting elongated rod structure that is fixed with one longitudinal end to the pressure housing and extends with an opposite longitudinal end into the gas storage portion. A self-supporting elongated rod structure is sufficiently stable to extend into the gas storage portion without getting in mechanical contact with the inside of the pressure housing. In other words, by means of a self-supporting elongated rod structure the porous storage medium can be exclusively fixed with only one end to the pressure housing while all other or residual outside-facing surface portions of the porous storage medium are located inside the gas storage portion thereby forming or constituting a boundary between the liquid storage portion and gas storage portion.

It is of particular benefit when the self-supporting elongated rod structure is exclusively connected to a closure of the pressure container. The closure is typically releasably attachable to the pressure housing to seal the interior volume thereof. By loosening and removing the closure from and out of the pressure housing, the porous storage medium fixed thereto can be taken out of the pressure housing. Such a configuration is of particular use for refilling of the pressure container. The closure may serve as a handle to displace or to remove the porous storage medium. For instance, the porous storage medium may be gripped by means of the closure and could be immersed into the liquid driving medium to soak and to absorb driving medium. Thereafter, the porous storage medium and the closure can be inserted into and affixed to the pressure housing, thereby arranging the porous storage medium at a predefined position inside the interior volume.

In another embodiment, the pressure container comprises a fluid channel in flow connection with the pressure outlet. The fluid channel extends from a sidewall portion of the pressure housing into the interior volume but terminates with an inner end in the gas storage portion. The fluid channel may be integrally formed with the pressure housing or may be provided as a separate part. Typically, the inner end of the fluid channel is located at a predefined distance to the sidewall as well as to a bottom or top portion of the pressure housing. Since the inner end of the fluid channel is located at a predefined distance from the wall structure of the pressure housing it is possible to implement a dynamic boundary between the liquid storage portion and the gas storage portion.

Hence, the interior volume of the pressure housing may be only partially filled with the liquid phase of the driving medium. But then the filling level should be reduced to such a degree that the surface of the liquid phase cannot get into contact with the inner end of the fluid channel irrespective on any orientation of the pressure housing. Hence, for any arbitrary orientation leading to different positions of the liquid phase the inner end of the fluid channel will be located at least at a predefined distance to the surface of the liquid phase of the driving medium.

According to a further embodiment, the inner end of the fluid channel is covered with a splash guard. In other words, as seen in longitudinal direction the inner end of the elongated fluid channel is closed by the splash guard. In order to provide ingress of the gas phase into the fluid channel the fluid channel has at least one inlet opening in a sidewall portion. By making use of a splash guard at the inner end of the fluid channel ingress of the liquid phase of the driving medium into the fluid channel can be effectively prevented, even in case that the pressure container should be subject to mechanical shock or vibrations.

Typically, the at least one or several inlet openings of the fluid channel is or are arranged in the sidewall portion thereof in close vicinity to the splash guard or to the inner end of the fluid channel. In this way, it can be assured that only the gas phase will be able to enter the fluid channel even when the pressure container is oriented upside down.

According to another embodiment, the porous storage medium or porous transport medium comprises at least one of a cotton wool, a sponge material, a porous wick material or combinations thereof. The porous storage medium may comprise a foamed structure. It may comprise or consist of a polymeric or synthetic material. Alternatively, the porous storage medium comprises or consists of a fiber material, a non-woven material or non-woven fabric.

The porous storage medium may be selected in accordance and in view of the driving medium. The porous storage medium may be selected on the basis of its median pore size and with regard to the surface tension of the driving medium.

According to another embodiment, the liquid storage portion of the interior of the portable pressure container is at least partially filled by a liquid phase of the driving medium. In particular, the pressure container is prefilled with the driving medium to such an extent, that the interior of the pressure housing is filled by an equilibrium of the liquid phase and the gas phase of the driving medium. A prefilled pressure container is particularly suitable as a disposable pressure container, which is intended to be discarded after use.

Certain aspects also relate to a pressure-driven portable medical device comprising a pressure-driven drive mechanism and comprising at least one pressure container as described above. Typically, the portable medical device is configured as an injection device for intradermal or subcutaneous injection of a liquid medicament. The medical device is particularly adapted and configured for releasable adhesion to the skin of a patient. The pressure container provides a source of energy that can be used to induce or to trigger a fully automated injection process starting with launching of a needle to penetrate or to pierce biological tissue, to optionally establish a fluid connection between an injection needle and a cartridge containing the liquid medicament, and to induce and to conduct injection of the liquid medicament into the biological tissue by a continuous or step-wise discharging of the medicament from the cartridge.

The term "drug" or "medicament", as used herein, means a pharmaceutical formulation containing at least one pharmaceutically active compound, wherein in one embodiment, the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment, the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment, the pharmaceutically active compound comprises at least one peptide for the treatment and/or prophylaxis of diabetes mellitus or complications associated with diabetes mellitus such as diabetic retinopathy, wherein in a further embodiment, the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-S er-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (02)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins, which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three on the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The pressure container provides a rather constant pressure level of a driving medium during the entire duration of an injection procedure. The portable pressure container is suitable for miniaturized medical devices, in particular to miniaturized injection devices that are intended to be carried along by a patient over a comparatively long time interval, such as several minutes or several hours. The portable pressure container provides a rather space-saving but also long-lasting source of mechanical energy for a pressure driven or pressure propelled injection device. Furthermore, the pressure container is easy to manufacture with a high degree of reproducibility at moderate or low costs. Moreover, the pressure container is storable in a configuration ready to use over a comparatively long time interval without a substantive degradation or dissipation of energy stored therein.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE FIGURES

In the following, embodiments of the drive mechanism and the injection device are described in detail by making reference to the drawings, in which.

DETAILED DESCRIPTION

Figure 6:
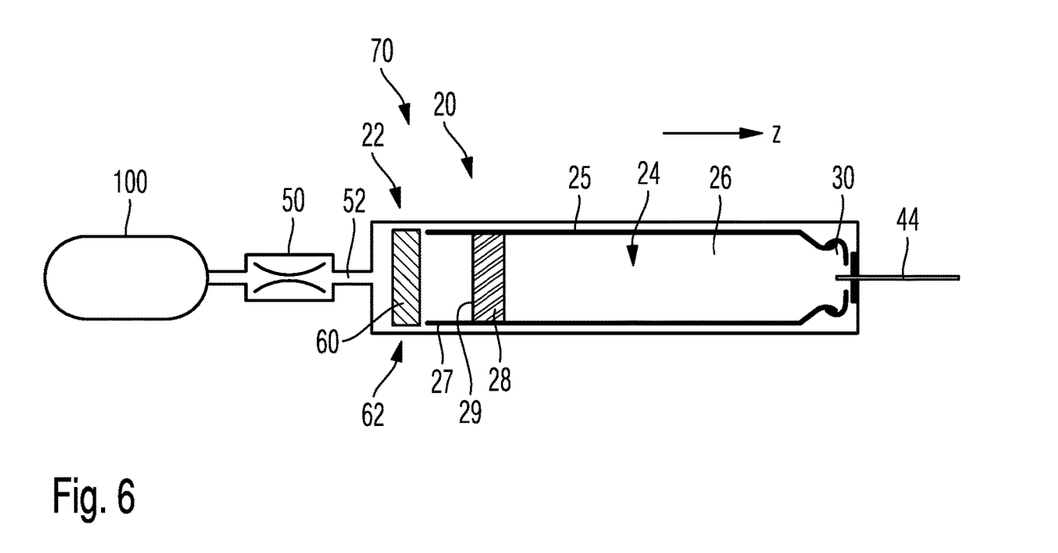

In FIG. 6, an injection device 20 is schematically illustrated. It comprises a housing 22, typically of tubular shape extending in an axial direction (z). Inside the housing 22 there is arranged a cartridge 24 comprising a tubular barrel 25 and being filled with a liquid medicament 26. Near a distal end the housing 22 is provided with a needle assembly having a cup-shaped needle hub and an injection needle 44 extending in longitudinal or axial direction (z). In distal direction, the injection needle faces away from the injection device 20. With its distal end, the injection needle 34 may penetrate or pierce biological tissue to deliver the liquid medicament 26. With its opposite proximal end facing in proximal direction, the injection needle 44 is configured to penetrate and to puncture a seal 30 at the distal end of the cartridge 24. The proximal end extends in proximal direction through an aperture of the distal end of the housing 22.

In the proximal direction, near a proximal end 27, the cartridge 24 is sealed by a piston 28 acting as a displaceable seal of the cartridge 24. The piston 28, typically of elastomeric material, such like a natural or synthetic rubber is displaceable in distal direction in order to expel a predefined amount of the medicament 26 via the injection needle 44, typically at a predefined flow rate. The piston 28 comprises a proximally-facing thrust receiving surface 29, which is subject to an increased pressure level. With the present injection device 20, a pressurized medium, such as a pressurized fluid or gas enters the proximal side of the housing 22 to apply a driving pressure to the piston 28.

For this, the housing 22 is in fluid connection or fluid communication with a pressure container 100 providing a medium, typically in form of a pressurized gas. In order to control the velocity of displacement of the piston 28 and to control the flow rate of the medicament 26 through the injection needle 44 there is further provided a flow restrictor 50, schematically illustrated in FIG. 6. The flow restrictor 50 is located in the flow path between the pressure container 100 and the piston 28. The injection device 20 further comprises a gas propelled drive mechanism 70 with a drive member 60, located inside the housing 22 proximal to the cartridge 24. The drive member 60 is in sealed engagement 62 with the inside of the sidewall of the housing 22. As soon as a pressurized gas enters the housing 22, the drive member in sealed engagement with the housing 22 will be urged in distal direction thereby pushing the entire cartridge 24 in distal direction. Consequently, the seal 30 at the cartridge's distal end will be pierced by the proximal tip of the double tipped injection needle 44, thereby gaining access to the interior of the cartridge 24. The cartridge has arrived in a distal end position inside the housing 22. In this configuration, the drive member 60 will be susceptible for the driving medium to get therethrough so that the pressurized gas is then able to drive the piston 28 of the cartridge 24 in a well defined and controlled way. Thus, the piston 28 moves in distal direction, thereby dispensing and expelling the medicament from the cartridge 24.

In FIGS. 1-5 various embodiments of pressure containers 100, 200, 300, 400, 500 are illustrated that are capable to provide a rather constant gas flow at a pressure outlet 102, 202, 302, 402, 502 provided in a pressure housing 101, 201, 301, 401, 501, wherein said pressure housing confines an interior volume 103, 203, 303, 403, 503. The various pressure containers 100, 200, 300, 400, 500 comprise a liquid storage portion 105, 205, 305, 405, 505 and a gas storage portion 104, 204, 304, 404, 504. The liquid storage portion 105, 205, 305, 405, 505 is configured to store and to accommodate a liquid phase 15 of a driving medium 10 whereas the gas storage portion 104, 204, 304, 404, 504 is configured to store or to accommodate a gas phase 14 of the driving medium 10.

As shown in FIGS. 1-5 the pressure outlet 102, 202, 302, 402, 502 is only or exclusively in flow connection or fluid communication with the gas storage portion 104, 204, 304, 404, 504 so that only the gas phase 14 of the driving medium 10 will be able to emanate or to escape from the pressure housing 101, 201, 301, 401, 501 through the pressure outlet 102, 202, 302, 402, 502.

In the various embodiments as shown in FIGS. 1-5, the pressure housing 101, 201, 301, 401, 501 is of substantially cylindrical or cubic rectangular shape. However, the pressure housing is by no way limited to the illustrated geometric forms. The pressure housing 101 could also have a spherical, oval or ellipsoidal shape. In the various embodiments of FIGS. 1-5, the pressure housing 101, 201, 301, 401, 501 comprises a bottom portion 107, 207, 307, 407, 507 and at least one sidewall 106, 206, 306, 406, 506 extending towards a top portion 108, 208, 308, 408, 508. In the illustrations according to FIGS. 1 and 2 the pressure container 100, 200 is rotated by 90° so that it is lying on its sidewall 106, 206.

Figure 1:
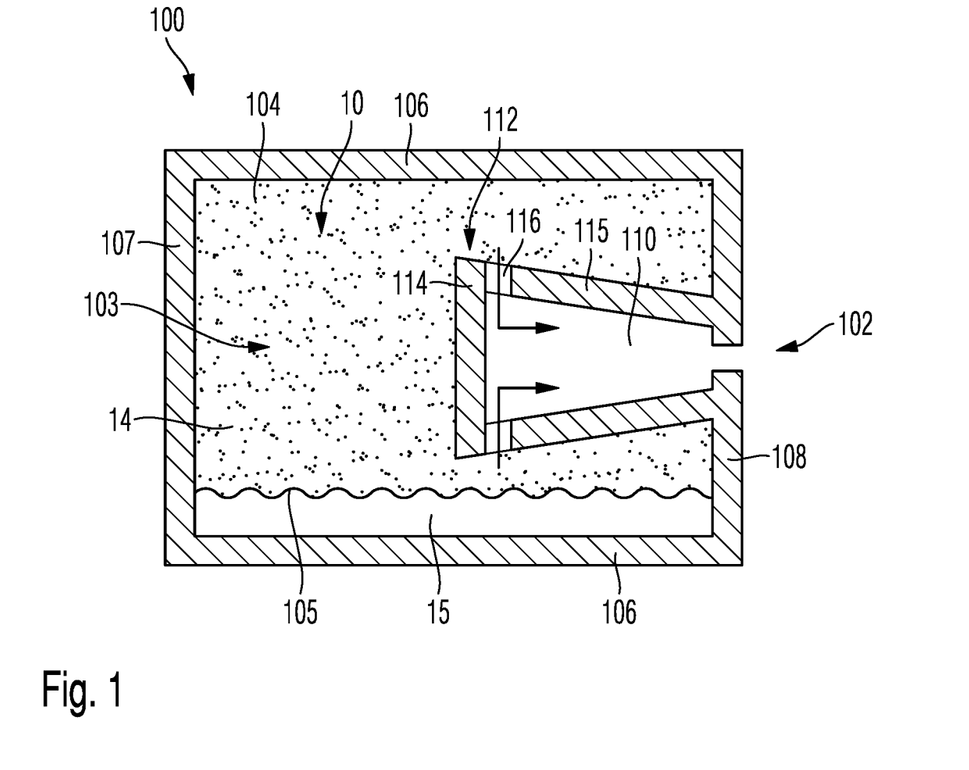
FIG. 1 is a cross section of one embodiment of the portable pressure container.

The pressure container 100, as shown in FIG. 1, comprises a fluid channel 110 in flow connection with the pressure outlet 102. The fluid channel 110 extends inwardly from the top portion 108 of the pressure housing 101 and into the interior 103 of the pressure housing 101. The fluid channel 110 formed by a conically or cylindrically-shaped sidewall 115 terminates at an inner end 112 that is located at a predefined distance from the sidewall 106, as well as from the bottom portion 107 and the top portion 108 of the pressure housing 101. The inner end 112 of the fluid channel 110 is further covered by a splash guard 114 so as to prevent ingress of the liquid phase 15 of the driving medium 10 into the fluid channel 110.

For the gas phase 14 to enter the fluid channel 110, there is provided at least one inlet opening 116 in the sidewall 115 of the fluid channel 110. As shown in FIG. 1 there are provided at least two inlet openings 116 that are located in direct vicinity to the splash guard 114 and that are hence located near the inner end 112 of the fluid channel 110. In this way, the liquid phase 15 of the driving medium 10 can be stored inside the interior volume 103 without being fixed in a particular region of the interior volume.

Hence, the boundary between the liquid phase 15 and the gas phase 14 of the driving medium 10 is of dynamic type and depends on the orientation of the portable pressure container 100 and the effect of the gravity on the liquid phase 15. In this embodiment, the interior volume 103 is only partially filled with the liquid driving medium so that the filling level of the liquid phase 15 never reaches or never gets in contact with the inlet openings 116 of the fluid channel 110. For instance, in a substantially vertical orientation, wherein the top part 108 is located on top and wherein the bottom portion 107 is a lower portion of the pressure housing 101, the filling level of the liquid phase 15 is smaller than the distance between the inner end 112 and the bottom portion 107.

In another orientation, in which the portable pressure container 100 is for instance oriented upside down so that the pressure outlet 102 is located at a lower portion, the filling level of the liquid phase 15 will be smaller than the distance between the inlet opening 116 and the top portion 108 of the pressure housing 101. In this way, it can be effectively guaranteed, that only the gas phase 14 discharges from the interior volume 103 irrespective of the momentary orientation of the portable pressure container 100.

Even though not particularly illustrated, the pressure outlets 102, 202, 302, 402, 502 of all embodiments as illustrated in FIGS. 1-5, may be provided with a standardized coupling or connector by way of which the pressure container 100, 200, 300, 400, 500 can be releasably connected to the medical device 20, and in particular to a gas-propelled drive mechanism 70 of the medical device 20.

Figure 2:
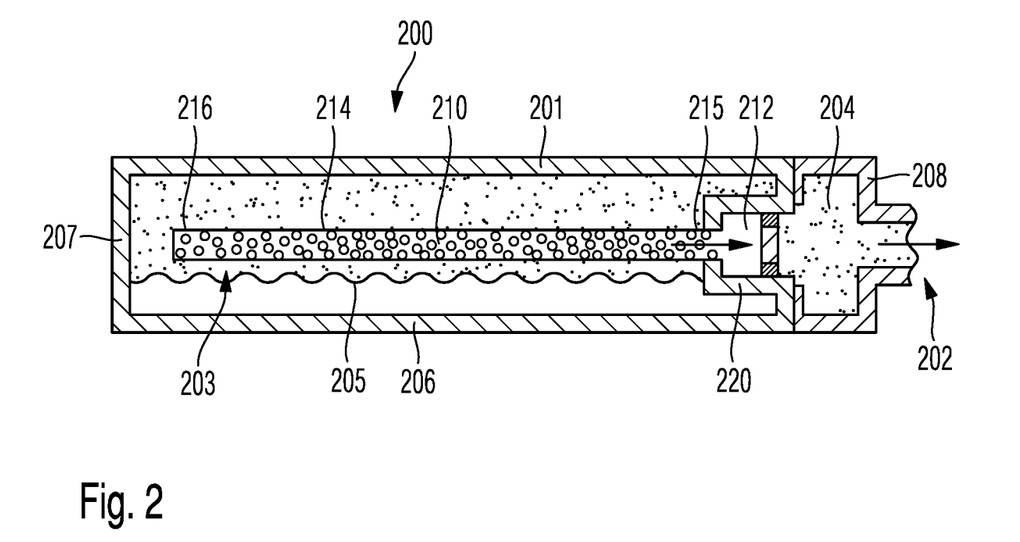
FIG. 2 is a cross section of another embodiment of the pressure container.

In the embodiment according to FIG. 2, a static configuration of the boundary between the liquid storage portion 205 and the gas storage portion 204 is illustrated. There, the gas storage portion 204 is located in direct vicinity to the top portion 208 of the pressure housing 202. It is separated and divided from the liquid storage portion 205 by a division wall 220. The division wall 220 is intersected by a porous transport medium 210. The porous storage medium 210 comprises an elongated rod structure 214 and is only and exclusively fixed to the pressure container 201 at the division wall 220. The portion where the rod structure 214 is connected to and intersects the division wall 220 acts as an evaporation chamber 212. The residual portion of the rod structure 214 is located inside the liquid storage portion 205. In this embodiment, the liquid storage portion 205 may be completely or almost completely filled with the liquid phase 15 of the driving medium 10. The porous transport medium 210 has pores of a particular size so that the liquid phase 15 of the driving medium 10 is continuously transported towards and into the evaporation chamber 212 through the capillary forces that arise due to the surface tension of the liquid phase 15 and the pore size of the porous transport medium 210.

The porous transport medium 210 is illustrated as a self-supporting elongated rod structure 214, which is only fixed with one longitudinal end 215 to the pressure housing 201 while an opposite longitudinal end 216 extends into the gas storage portion 204. Having a self-supporting and rather inflexible rod structure 214 is somewhat beneficial to assure that the porous transport medium 210 does not adhere to the inside of the sidewall 206 of the pressure housing 201. However, it is also conceivable that the porous transport medium 210 is of flexible type. It may comprise a natural or synthetic wick material to provide transportation of the liquid phase towards the evaporation chamber 212.

Figure 3:
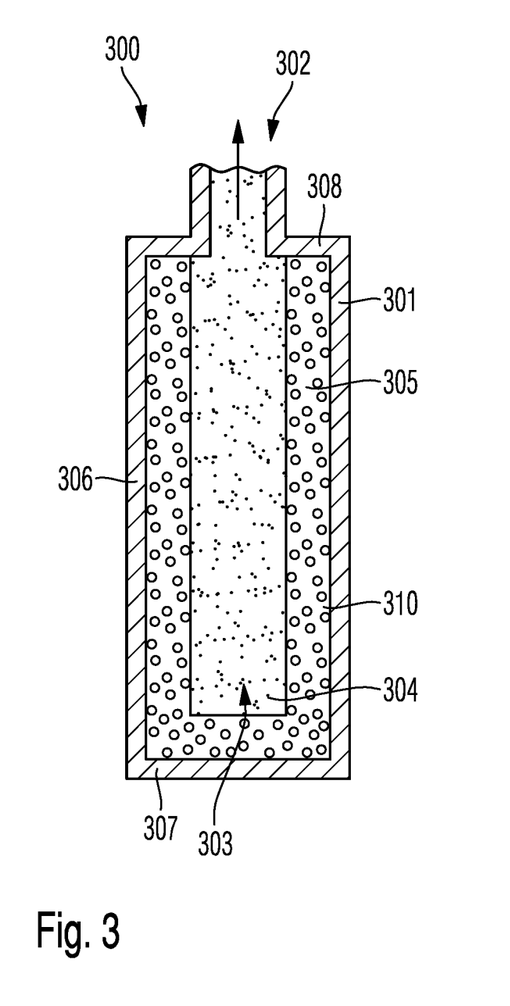
FIG. 3 is a cross section through a further embodiment of the pressure container.

In a further embodiment of the portable pressure container 300 as shown in FIG. 3, there is provided a porous storage medium 310 that is arranged along the inside of the pressure housing 301. As shown in the cross section according to FIG. 3 the porous storage medium 310 entirely covers the bottom portion 307 as well as the sidewall or sidewall portions 306 of the pressure housing 301. It may even abut with the top portion 108 in direct vicinity to the sidewalls 106. Only the region or the vicinity of the pressure outlet 302 is free of the porous storage medium 310.

In this way, the gas storage portion 304 is almost completely enclosed by the liquid storage portion 305. The boundary between the gas storage portion 304 and the liquid storage portion 305 is static and is determined by the geometric dimensions of the porous storage medium 310. The arrangement of the porous storage medium 310 to the sidewall 306 and to the bottom portion 307 is beneficial for a thermal coupling of the liquid storage portion 105 to the exterior. When establishing for instance a thermal coupling between the pressure housing 310 and the skin of a patient, evaporation enthalpy for a continuous transfer of the liquid phase 15 into the gas phase 14 during use of the pressure container 300 can be extracted from the body heat.

Figure 4:
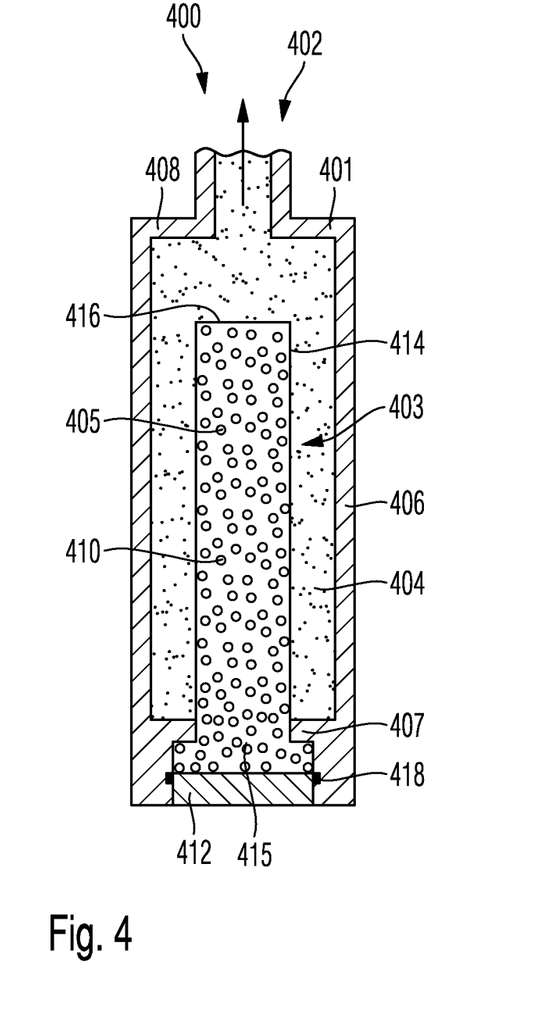
FIG. 4 is a cross section through another embodiment of the pressure container.
Figure 5:
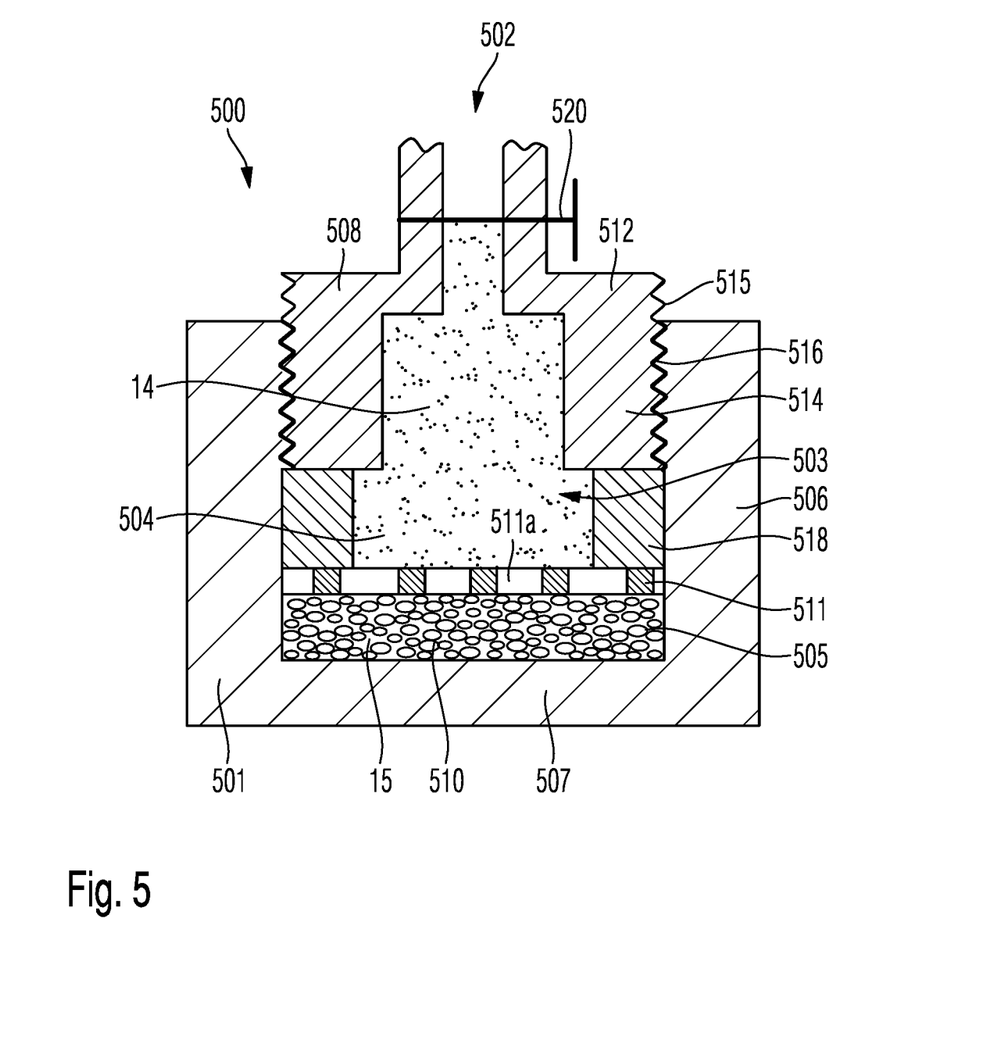
FIG. 5 is a cross section through a further embodiment of the pressure container and FIG. 6 is a schematic illustration of a pressure-driven portable medical device comprising a pressure container in accordance with one of the embodiments of FIGS. 1-5.

In the embodiments as shown in FIGS. 3, 4, and 5, the liquid storage portion 305, 405, 505 is defined by the geometric dimensions of the porous storage medium 310, 410, 510. Typically, the porous storage medium 310, 410, 510 may comprise or consist of a cotton wool, a sponge material, a porous wick material, as well as variable natural or synthetic porous media exhibiting a pore size and a pore volume or pore density to maximize the storage capability of the liquid phase per volume.

In the further embodiment as shown in FIG. 4, the porous storage medium 410 is connected to a closure 412 that is configured to be releasably attached to the bottom portion 407 of the pressure housing 401. Here, the porous storage medium 410 comprises a self-supporting rod structure 414 extending into the interior volume 403 confined by the pressure housing 401. Besides a contact with the bottom portion 407 and a contact with the closure 412, the porous storage medium 410 is totally contactless to the inside of the pressure housing 401. Hence, FIG. 4 represents an inverted configuration compared to the embodiment as shown in FIG. 3. Here, the gas storage portion 404 almost completely surrounds the liquid storage portion 405 that is defined by the geometric dimensions of the porous storage medium 410. The rod structure 414 of the porous storage medium 410 is connected with one longitudinal end 415 to the closure 412 whereas an opposite longitudinal end 416, hence the free end 416 of the rod structure 414, is located inside the interior volume 403 of the pressure housing 401. It is located at a predefined distance from the top portion 408 of the pressure housing 401 for not hindering the flow of the gas phase towards the pressure outlet 402.

The closure 412 may be of releasable or detachable type. It may be for instance threadedly engageable with the bottom 407 of the pressure housing 401. At least one of the closure 412 or the pressure housing 401 comprises a seal 418, typically in form of an O-ring, in order to provide a leak-proof closure assembly. The embodiment as shown in FIG. 4, is particularly suitable to provide a refill of the portable pressure container 400. By detaching and removing the closure 412, the porous storage medium 410 is detachable from the interior volume 403. It may be immersed in a liquid phase 15 of the driving medium 10 to saturate the porous storage medium 410. Thereafter, the porous storage medium 410 may be re-inserted into the interior volume 403 and the closure 412 may seal the pressure housing 401.

The further embodiment as shown in FIG. 5, comprises a cup-shaped pressure housing 501 having an interior volume 503 that is delimited and confined by a planar-shaped bottom portion 507 and a cylindrical sidewall 506. An upper portion of the inside of the cylindrical sidewall 506 is provided with an inner thread 516 to threadedly engage with an outer thread 515 of an outlet member 512 comprising the pressure outlet 502. The pressure outlet 502 is further provided with an outlet valve 520, which may be implemented as a commercially available ball valve or the like.

The cup-shaped pressure housing is closed by the outlet member 512. The cylindrically-shaped sidewall 514 of the outlet member 512 is configured to match with the inner diameter of the sidewall 506 of the pressure housing 501 to establish a threaded and releasable connection of the cup-shaped pressure housing 501 and the outlet member 512. Inside the pressure housing 501, there is provided a porous storage medium 510 covering the entirety of the planar-shaped bottom portion 507. On top of the porous storage medium 510, there is provided and positioned a perforated grid 511 having numerous perforations 511a that allow evaporation of the liquid phase 15 into the gas phase 14. The perforated grid 511 provides mechanical stability to the porous storage medium 510 and keeps the porous storage medium 510 in place at the bottom portion 507.

There is further provided a distance member 518 or spacer that has an outer circumference that matches with the inner circumference of the sidewall 506 of the cup-shaped pressure housing 501. An upper portion of the distance member 518 is in axial abutment with a lower face of the outlet member 512. In this way, the outlet member 512 is mechanically engageable with the perforated grid 511 as well as with the porous storage medium 510. By screwing the outlet member 512 further into the cup-shaped pressure housing 501, a pressure can be applied to the perforated grid 511 and to the porous storage medium 510 via the distance member 518.

Typically and in order to provide a sufficient sealing effect, the threaded engagement between outer thread 515 of the outlet member 512 and the inner thread 516 of the sidewall 506 is provided with a sealing tape, e.g. of polytetrafluoroethylene (PTFE). The cup-shaped pressure housing 501, as well as the pressure housings 101, 201, 301, 401, may comprise a transparent material, such like polycarbonate or similar plastic but durable materials that allow visual inspection of the interior of the portable pressure container 100, 200, 300, 400, 500.

The size of the perforations 511a of the perforated grid 511 may be in a range of 1 or 2 mm so as to provide sufficient mechanical stability to the porous storage medium 510 and to allow a sufficient evaporation rate and a respective gas flow from the liquid phase 15 towards the gas phase 14.

The distance member 518 may comprise a piece of a hose and the perforated grid 511 may comprise a plastic material, which may either be injection molded, cut or punched to provide a desired perforated structure.

The driving medium may comprise a haloalkane such like tetrafluoromethane or similar driving media. For instance, the driving medium may comprise or consist of 1,1,1,2-tetrafluoroethane, also denoted as R134a. Likewise, also 2,3,3,3-tetrafluoropropene, also denoted as HFO-1234yf and mixtures thereof with at least one of the aforementioned driving medias can be used as the driving medium. These driving medias are gaseous at room temperature but may easily undergo a phase transition to the liquid phase if sufficiently pressurized or heated.

LIST OF REFERENCE NUMBERS 10 driving medium
14 gas phase
15 liquid phase
20 medical device
22 housing
24 cartridge
25 barrel
26 medicament
27 proximal end
28 piston
29 thrust receiving surface
30 seal
44 injection needle
50 flow restrictor
60 drive member
62 sealed engagement
70 drive mechanism
100 pressure container
101 pressure housing
102 pressure outlet
103 interior volume
104 gas storage portion
105 liquid storage portion
106 sidewall
107 bottom portion
108 top portion
110 fluid channel
112 inner end
114 splash guard
115 sidewall
116 inlet opening
200 pressure container
201 pressure housing
202 pressure outlet
203 interior volume
204 gas storage portion
205 liquid storage portion
206 sidewall
207 bottom portion
208 top portion
210 porous transport medium
212 evaporation chamber
214 rod structure
215 longitudinal end
216 longitudinal end
220 division wall
300 pressure container
301 pressure housing
302 pressure outlet
303 interior volume
304 gas storage portion
305 liquid storage portion
306 sidewall
307 bottom portion
308 top portion
310 porous storage medium
400 pressure container
401 pressure housing
102 pressure outlet
403 interior volume
404 gas storage portion
405 liquid storage portion
406 sidewall
407 bottom portion
408 top portion
410 porous storage medium
412 closure
414 rod structure
415 longitudinal end
416 longitudinal end
418 seal
500 pressure container
501 pressure housing
502 pressure outlet
503 interior volume
504 gas storage portion
505 liquid storage portion
506 sidewall
507 bottom portion
508 top portion 510 porous storage medium
511 perforated grid
511a perforation
512 outlet member
514 sidewall
515 outer thread
516 inner thread
518 distance member
520 outlet valve

The invention claimed is:

1. A portable pressure container for driving a medical device, the container comprising:
 a pressure housing confining an interior volume,
 a pressure outlet extending through the pressure housing,
  wherein the interior volume comprises a liquid storage portion and a gas storage portion, wherein the liquid storage portion and the gas storage portion are in flow connection with each other,
  wherein the liquid storage portion is configured to store a liquid phase of a driving medium and wherein the gas storage portion is configured to store a gas phase of the driving medium,
  wherein the pressure outlet is only in direct flow connection with the gas storage portion,
  wherein the liquid storage portion is located remote and at a predefined non-zero distance from the pressure outlet and wherein the gas storage portion is located between the liquid storage portion and the pressure outlet, and
  wherein a porous storage medium or a porous transport medium is arranged inside the liquid storage portion and extends towards or into the gas storage portion.

2. The pressure container according to claim 1, wherein the porous storage medium is in abutment with an inner side of the pressure housing.

3. The pressure container according to claim 1, wherein the porous storage medium and the pressure outlet are arranged in opposite end sections of the pressure housing.

4. The pressure container according to claim 1, wherein the porous storage medium is arranged on a bottom portion of the pressure housing and is held in place or squeezed by a perforated grid.

5. The pressure container according to claim 1, wherein the pressure outlet is located in an outlet member releasably engageable with the pressure housing.

6. The pressure container according to claim 5, wherein the outlet member comprises a side wall threadedly engageable with a correspondingly threaded side wall portion of the pressure housing to exert a squeezing pressure onto the porous storage medium.

7. The pressure container according to claim 1, wherein the porous storage medium extends along a bottom portion and along a sidewall portion of the pressure housing.

8. The pressure container according to claim 1, wherein the porous storage medium comprises a self-supporting elongated rod structure fixed with one longitudinal end to the pressure housing and extending with an opposite longitudinal end into.

9. The pressure container according to claim 1, wherein the porous storage medium or porous transport medium comprises at least one of a cotton wool, a sponge material, a porous wick material or combinations thereof.

10. The pressure container according to claim 1, further comprising a fluid channel in flow connection with the pressure outlet and extending from a sidewall portion of the pressure housing into the interior volume but terminating with an inner end in the gas storage portion.

11. The pressure container according to claim 10, wherein the inner end of the fluid channel is covered with a splash guard and wherein the fluid channel has at least one inlet opening in a sidewall portion.

12. The pressure container according to claim 1, wherein the liquid storage portion is at least partially filled by a liquid phase of the driving medium.

13. The pressure container according to claim 1, wherein the interior volume of the pressure housing is divided between the liquid storage portion and the gas storage portion.

14. The pressure container according to claim 1, wherein the driving medium is disposed in the interior volume of the pressure housing, wherein the liquid storage portion is completely filled by the liquid phase of the driving medium and wherein the gas storage portion is completely filled by the gas phase of the driving medium.

15. A pressure driven portable medical device comprising a pressure driven drive mechanism and comprising at least one pressure container, the pressure container comprising:
 a pressure housing confining an interior volume,
 a pressure outlet extending through the pressure housing,
  wherein the interior volume comprises a liquid storage portion and a gas storage portion, wherein the liquid storage portion and the gas storage portion are in flow connection with each other,
  wherein the liquid storage portion is configured to store a liquid phase of a driving medium and wherein the gas storage portion is configured to store a gas phase of the driving medium,
  wherein the pressure outlet is only in direct flow connection with the gas storage portion,
  wherein the liquid storage portion is located remote and at a predefined non-zero distance from the pressure outlet and wherein the gas storage portion is located between the liquid storage portion and the pressure outlet, and
  wherein a porous storage medium or a porous transport medium is arranged inside the liquid storage portion and extends towards or into the gas storage portion.

\* \* \* \* \*